United States Patent
Podola et al.

(10) Patent No.: US 12,305,161 B2
(45) Date of Patent: *May 20, 2025

(54) **METHOD OF CULTURING *HAEMATOCOCCUS* SPECIES FOR MANUFACTURING OF ASTAXANTHIN**

(71) Applicant: AD ASTRA EHF, Kopavogur (IS)

(72) Inventors: Björn Podola, Cologne (DE); Michael Melkonian, Lohmar (DE); Alice Costa Kiperstok, Cologne (DE); Petra Sebestyen, Nagykörös (HU)

(73) Assignee: AD ASTRA EHF, Kopavogur (IS)

( * ) Notice: Subject to any disclaimer, the term of this patent is extended or adjusted under 35 U.S.C. 154(b) by 0 days.

This patent is subject to a terminal disclaimer.

(21) Appl. No.: 17/370,849

(22) Filed: Jul. 8, 2021

(65) Prior Publication Data

US 2021/0340489 A1 Nov. 4, 2021

Related U.S. Application Data

(63) Continuation of application No. 15/758,143, filed as application No. PCT/EP2016/071270 on Sep. 9, 2016, now Pat. No. 11,085,014.

(30) Foreign Application Priority Data

Sep. 11, 2015 (EP) ..................................... 15184899

(51) Int. Cl.
*C12N 1/12* (2006.01)
*C12P 23/00* (2006.01)

(52) U.S. Cl.
CPC ................ *C12N 1/12* (2013.01); *C12P 23/00* (2013.01); *C12N 2529/10* (2013.01)

(58) Field of Classification Search
CPC .................................. C12N 1/12; C12N 23/00
See application file for complete search history.

(56) References Cited

U.S. PATENT DOCUMENTS

2007/0092932 A1  4/2007  Zhang
2008/0254056 A1  10/2008 Zhang

FOREIGN PATENT DOCUMENTS

| EP | 1760157 A1 | 3/2007 |
| JP | 2007-097584 A | 4/2007 |
| KR | 2014-0075869 A | 6/2014 |
| WO | 2005/010140 A1 | 2/2005 |
| WO | 2005/116238 A1 | 12/2005 |
| WO | 2007/029627 A1 | 3/2007 |

OTHER PUBLICATIONS

Fábregas et al., Appl Microbiol Biotechnol., 2000, 53: 530-535.*
Wan et al. Bioresource Technology, 2014, 163:26-32.*
Ozkan et al. Bioresource Technology, 2012, 114:542-548.*
International Search Report and Written Opinion in International Patent Application No. PCT/EP2016/071270, Aug. 11, 2016.
Aflalo et al., "On the Relative Efficiency of Two- vs. One-stage Production of Astaxanthin by the Green Alga *Haematococcus pluvialis*," Biotechnol Bloeng 98:300-305. doi: 10.1002/bit.21391 (2007).
Benstein et al., "Immobilized Growth of the Peridinin-Producing Marine Dinoflagellate Symbiodinium in a Simple Biofilm Photobioreactor," Marine Biotechnology, vol. 16, No. 6, pp. 621-628 (Dec. 2014).
Berner et al., "Microalgal biofilms for biomass production," J Appl Phycol. vol. 27, pp. 1793-1804. doi: 10.1007/s10811-014-0489-x (2014).
Del Rio et al., "Efficiency assessment of the one-step production of astaxanthin by the microalga *Haematococcus pluvialis*" Biotechnology and Bioengineering, (2008) vol. 100, No. 2, pp. 397-402.
Del Rio et al., "Efficient one-step production of astaxanthin by the microalga *Haematococcus pluvialis* in continuous culture," Biotechnol. Bioeng. 91:808-815. doi: 10.1002/bit.20547 (2005).
Dong et al., "Four Different Methods Comparison for Extraction of Astaxanthin from Green Alga *Haematococcus pluvialis*," Scientific World Journal Article ID 694305 (2014).
Esperanza et al., "Efficient one-step production of astaxanthin by the microalga *Haematococcus pluvialis* in continuous culture," Biotechnology and Bioengineering, vol. 91, No. 7, pp. 808-815 (Sep. 2005).
Fiedler et al., "Algae biocers: astaxanthin formation in sol-gel immobilised living microalgae", J. Mater. Chem., vol. 17, pp. 261-266 (2007).
Garcia-Malea et al., "Production of Astaxanthin by Haematococcus pluvialis: Taking the one-Step System Outdoors", Biotechnology and Bioengineering, vol. 102, No. 2, pp. 651-657 (2009).
Jiang et al., "Effect of Light Stress on Astaxanthin Accumulation and Antioxidant Activity of Haematococcus Pluvialis", Modern Food Technology, vol. 31, Issue 10, pp. 215-221, 233 (2015).
Zhang et al., "Attached cultivation for improving the biomass productivity of Spirulina platensis," Bioresour. Technol., 181:136-142. doi: 10.1016/j.biortech.2015.01.025 (2015).
Wang et al., "Combined effect of initial biomass density and nitrogen concentration on growth and astaxanthin production of," Algae 28:193-202 (2013).
Kiperstok, "Optimizing immobilized cultivation of Haematococcus pluvialis for astaxanthinproduction," pp. 1-128 (Apr. 2016), retrieved from the Internet <http://kups.ub.uni-koeln.de/6728/1/KIPERSTOK_PhD_Thesis_Final_Version.pdf>.

(Continued)

*Primary Examiner* — Vera Afremova
(74) *Attorney, Agent, or Firm* — Venable LLP; Keith G. Haddaway; Hermant Khanna

(57) ABSTRACT

A method of culturing *Haematococcus* species for manufacturing of astaxanthin comprising the steps of: providing a substrate, arranging the *Haematococcus* species on the surface of the substrate, exposing the *Haematococcus* species arranged on the substrate to high light intensities from the beginning of a culturing process and avoiding a two-step culturing process of the *Haematococcus* species with a first step which is an initial culturing taking place by exposure of the *Haematococcus* species to low light energy followed by a second step of subsequent culturing of the *Haematococcus* species by exposure of the *Haematococcus* species to higher light energy than applied in the first step to induce astaxanthin formation, and optionally—harvesting the cultured *Haematococcus* species and/or—isolating astaxanthin.

10 Claims, 2 Drawing Sheets

(56) References Cited

OTHER PUBLICATIONS

Li et al., "Accurate quantification of astaxanthin from Haematococcus crude extract spectrophotometrically," Chinese J. Oceanol. Limnol., 30:627-637. doi: 10.1007/s00343-012-1217-5 (2012).

Lu et al., "Attached cultivation technology of microalgae for efficient biomass feedstock production," Bioresource Technology 127:216-222. doi: 10.1016/j.biortech.2012.09.100 (2013).

López et al., "Comparative analysis of the outdoor culture of Haematococcus pluvialis in tubular and bubble column photobioreactors," J. Biotechnol. 123:329-342. doi: 10.1016/j.jbiotec.2005.11.010 (2006).

Lorenz et al., "Commercial potential for Haematococcus microalgae as a natural source of astaxanthin," Trends Biotechnol 18:160-167 (2000).

Murphy et al., "A Novel Microbial Cell Cultivation Platform for Space Applications," In: 1st Annual International Space Station Research and Development Conference. Denver, CO: American Astronomical Society (AAS), pp. 335-339 (2012).

Yin et al., "The water footprint of biofilm cultivation of Haematococcus pluvialis is greatly decreased by using sealed narrow chambers combined with slow aeration rate," Biotechnol. Lett. 37:1819-1827. doi: 10.1007/s10529-015-1864-7 (2015).

Naumann et al., "Growing microalgae as aquaculture feeds on twin-layers: a novel solid-state photobioreactor," Journal of Applied Phycology, vol. 25, No. 5, pp. 1413-1420 (Dec. 2012).

Nguyen, "Astaxanthin: a comparative case of synthetic vs. natural production," Chem. Biomol. Eng. Publ. Other Work 1:1-11 (2013).

Nobre et al., "Supercritical carbon dioxide extraction of astaxanthin and other carotenoids from the microalga *Haematococcus pluvialis*," European Food Research and Technology, 223, 787-790. Retrieved from http://dx.doi.org/10.1007/s00217-006-0270-8 (2006).

Nowack et al., "The 96-well Twin-Layer system: A novel approach in the cultivation of microalgae," Protist 156:239-251. doi: 10.1016/j.protis.2005.04.003 (2005).

Office Action issued in corresponding Chinese Patent Application No. 2016800528556 on Dec. 3, 2020.

Olivieri et al., "Advances in photobioreactors for intensive microalgal production: configurations, operating strategies and applications," J Chem Technol Blotechnol 89:178-195. doi: 10.1002/jctb.4218 (2014).

Ozkan et al., "Reduction of water and energy requirement of algae cultivation using an algae biofilm photobioreactor," Bioresource Technology 114:542-548. doi: 10.1016/j.biortech.2012.03.055 (2012).

Schultze et al., "High light and carbon dioxide optimize surface productivity in a Twin-Layer biofilm photobioreactor," Algal Res 8C:37-44. doi: 10.1016/j.algal.2015.01.007 (2015).

Suh et al., "A novel double-layered photobioreactor for simultaneous Haematococcus pluvialis cell growth and astaxanthin accumulation," J. Biotechnol. 125:540-546. doi: 10.1016/j.jbiotec.2006.03.027 (2006).

Wan et al., "The effective photoinduction of Haematococcus pluvialis for accumulating astaxanthin with attached cultivation," Bioresource Technology, vol. 163, pp. 26-32 (Jul. 2015), 2014.

Kiperstock et al., "Biofilm cultivation of Haematococcus pluvialis enables a highly productive one-phase process for astaxanthin production using high light intensities", Algal Research, (Dec. 6, 2016), vol. 21, pp. 213-222, XP055834746; Retrieved from the Internet: URL:https://reader.elsevier.com/reader/sd/pii/S2211926416305094X?token=D79DF43E22A4B97DBD629A5F52B300DBF092DD57967211D4F027FC79217754699DC272DE7D878098D387C5C2D75D1762&originRegion=eu-west-1&originCreation=20210825080108 (retrieved on Aug. 25, 2021].

Extended European Search Report issued in corresponding European Application No. 21162642.9 on Sep. 8, 2021.

Imamoglu et al., "Influences of different stress media and high light intensities on accumulation of astaxanthin in the greeen alga *Haematococcus pluvialis*", New Biotechnology, (Oct. 2009), vol. 26, Nos. 3/4, pp. 199-204.

Zhang et al., "Attached cultivation of *Haematococcus pluvialis* for astaxanthin production", Bioresource Technology, (2014), vol. 158, pp. 329-335.

* cited by examiner

METHOD OF CULTURING *HAEMATOCOCCUS* SPECIES FOR MANUFACTURING OF ASTAXANTHIN

This application is a continuation of U.S. patent application Ser. No. 15/758,143, filed Mar. 7, 2018, now-U.S. Pat. No. 11,085,014, issued Aug. 10, 2021, which is a National Stage Application under 35 U.S.C. § 371 of International Application No. PCT/EP2016/071270, filed Sep. 9, 2016, which claims priority benefit from European Patent Application No. 15184899.1, filed Sep. 11, 2015, the content of each are incorporated herein by reference in their entirety.

A method of culturing *Haematococcus* species for manufacturing of astaxanthin. The present invention pertains to an improved method of culturing *Haematococcus* species for manufacturing of astaxanthin.

The microalga *Haematococcus pluvialis* is known by its secondary metabolic compound, namely astaxanthin, which has a high pigmentation and antioxidant capacity. Its coloring characteristic is mostly used for aquaculture in order to increase the pinkish color of salmon and shrimp flesh (Lorenz & Cysewski 2000). As an antioxidant agent, astaxanthin is marketed as a human health supplementary product (see AstaReal, Algatechnologies Ltd, Cyanotech Ltd, Nutrex Hawaii Ltd, Fuji Health Science Inc.). The major source of astaxanthin, nowadays, is the chemical synthesis (see CARDAX and BASF, only allowed for animal feed purposes).

However, astaxanthin from natural sources is gaining an increased interest and possesses a high value, due to several studies that show a better bioavailability and antioxidant capacity and the general preference of consumers towards natural or "bio" products (Nguyen 2013).

Nonetheless, the production of astaxanthin by *H. pluvialis* is still an expensive and challenging technology. To some extent, this is based on the fact that astaxanthin production by *H. pluvialis* occurs usually when cell division is ceased. Astaxanthin production is induced by certain stress factors, such as a high light intensity (over 200 µmol photons $m^{-2}$ $s^{-1}$), salt stress and nutrient deficiency (Aflalo et al. 2007).

Therefore, state-of-the-art cultivation methods consist of two phases: (i) a "green phase", where the cultivation parameters are optimal for production of a high cell density to provide sufficient biomass (light intensity: 50-200 µmol photons $m^{-2}s^{-1}$; temperature: 20-25° C.; pH 6.5-8); and (ii) a "red" phase where stress is applied to enhance astaxanthin production and accumulation, accompanied by significant reduction or cessation of cell division. Consequently, with a view on astaxanthin as a product, established technologies suffer from a non-productive green phase which contributes to about 50% of the total production period (Suh et al. 2006; Aflalo et al. 2007). Furthermore, a two-step procedure requires a higher technical effort by the requirement for two separate bioreactor systems: To provide low light intensities, the green phase is mostly located indoors, illuminated with artificial light sources avoiding photochemical stress, whereas the red phase benefits from high solar irradiances as found in outdoor photobioreactors.

Besides the obvious drawbacks of a discontinuous two-phase method, the state of the art cultivation systems are based on suspension growth in tubular reactors and open ponds (Lorenz and Cysewski 2000). However, these systems are well-known to have high costs for e.g. construction, operation and maintenance (Ozkan et al. 2012). Recent advances in bioreactor design demonstrated that biofilm-based bioreactors offer the potential to overcome some of these drawbacks of suspension-type bioreactors (e.g. Berner et al. 2014). In particular, *H. pluvialis*, was successfully grown in biofilms using porous substrate bioreactors at low light intensities (Wan et al. 2014; Yin et al. 2015; Zhang et al. 2014). Astaxanthin formation has also been described in sol-gel immobilized living microalgae (Fiedler et al 2007).

An object of the present invention is to provide an improved astaxanthin production by using biofilm (immobilized) cultivation of *Haematococcus* in a one-step procedure making use of high light intensities to increase biomass productivity and to induce and increase astaxanthin production. Another object of the invention is to avoid the drawbacks of the two-step procedure of the state of the art.

SUMMARY OF THE INVENTION

The object underlying the invention is solved by a method of culturing *Haematococcus* species for manufacturing of astaxanthin comprising the steps of:
providing a substrate,
arranging the *Haematococcus* species on the surface of the substrate, exposing the *Haematococcus* species arranged on the substrate to high light intensities from the beginning of a culturing process and avoiding a two-step culturing process of the *Haematococcus* species with a first step which is an initial culturing taking place by exposure of the *Haematococcus* species to low light energy followed by a second step of subsequent culturing of the *Haematococcus* species by exposure of the *Haematococcus* species to higher light energy than applied in the first step to induce astaxanthin synthesis;
optionally harvesting the cultured *Haematococcus* species; and/or
isolating the astaxanthin.

The invention is based on the unexpected finding that it is not mandatory to generate sufficient amount of cell mass of *Haematococcus* species in a first step (green phase) under low-light exposure and upon formation of sufficient amount of cell mass to induce astaxanthin formation at high light intensities.

In contrast to the cultivation of *Haematococcus* species in particular *H. pluvialis* according to the state of the art which is a two-step cultivation, the manufacturing method of the present invention provides for a one-step cultivation of both biomass and astaxanthin under high light intensities coupled with low maintenance and harvesting costs in particular provided by the application of a biofilm photobioreactor.

According to the invention the term high light intensities is understood by the skilled person not as a relative term but as a concrete one e.g. equivalent to at least about 150, 200, 250 or 500 µmol photons $m^{-2}s^{-1}$ or more.

Stress factors are enviromental influences which induce astaxanthin production in *Haematococcus* species in particular *H. pluvialis*, such as light intensities above 150 µmol photons $m^{-2}s^{-1}$, salinity (0.8% NaCl), temperatures higher than 30° C. and nutrient starvation in particular nitrogen and phosphorus but other deficiencies can also play a role. In particular, astaxanthin content in cells of *Haematococcus* species in particular *H. pluvialis* grown in biofilms as described here can still be increased by about 50% when subjecting the cells to media containing no nitrogen or phosphorus source in addition to high light intensities. In the same setting, the total astaxanthin productivity per growth surface can still be increased up to approximately 15% by application of nitrogen and/or phosphorus depletion.

The light which is used for culturing *H. pluvialis* is regularly in the UV and visible range of 300 nm to 780 nm.

Some data exist on biomass production of *H. pluvialis* at high light intensity (around 1,000 µmol photons $m^{-2}$ $s^{-1}$), however astaxanthin accumulation is low and only occurs when high light is coupled with nutrient limitation (Del Rio et al. 2005; Garcia-Malec López et al. 2006). According to the invention the whole cultivation process can be performed in one-step under high intensities of (natural) illumination, and, depending on the harvesting method, it can be optimized for a continuous production process with high biomass productivity, high astaxanthin content and high astaxanthin productivity. Over 10 days at a light intensity of 785 µmol photons $m^{-2}$ $s^{-1}$, biomass productivity can be as high as 16 g dry matter $m^{-2}d^{-1}$, with an astaxanthin content of 2-2.5% of dry matter. Thus the astaxanthin productivity can reach 0.39 mg $m^{-2}$ $d^{-1}$. In conventional two-step approaches, these values tend to be lower even if only for the second step, namely, the red-phase. A more exact calculation considering the entire period for both steps would be even lower, as observed by Wang et al. (2013).

In one embodiment of the invention the *Haematococcus* species is *Haematococcus pluvialis*. The invention will be further described by reference to *H. pluvialis*. The skilled person understands that the disclosure related to *H. pluvialis* is also valid for other species of *Haematococcus* which are able to produce astaxanthin.

In another embodiment of the invention the low light energy in the first step (green phase) is about 50 µmol photons $m^{-2}$ $s^{-1}$ to less than about 200 µmol photons $m^{-2}$ $s^{-1}$.

In still another embodiment the higher light energy in the second step (red phase) is at least about 200 µmol photons $m^{-2}$ $s^{-1}$ in particular at least about 500 µmol photons $m^{-2}$ $s^{-1}$.

In another embodiment of the invention *Haematococcus* is cultivated on the surface of a material (substrate).

In yet another embodiment of the invention the material is a sheet-like material.

In another embodiment of the invention the sheet-like material is porous.

In a further embodiment of the invention the sheet-like material is selected from the group consisting of paper, cellulose ester, in particular cellulose acetate, mixed cellulose ester, cellulose, cellulose nitrate, polyamides, polyesters and/or polyolefines.

Figure 3:
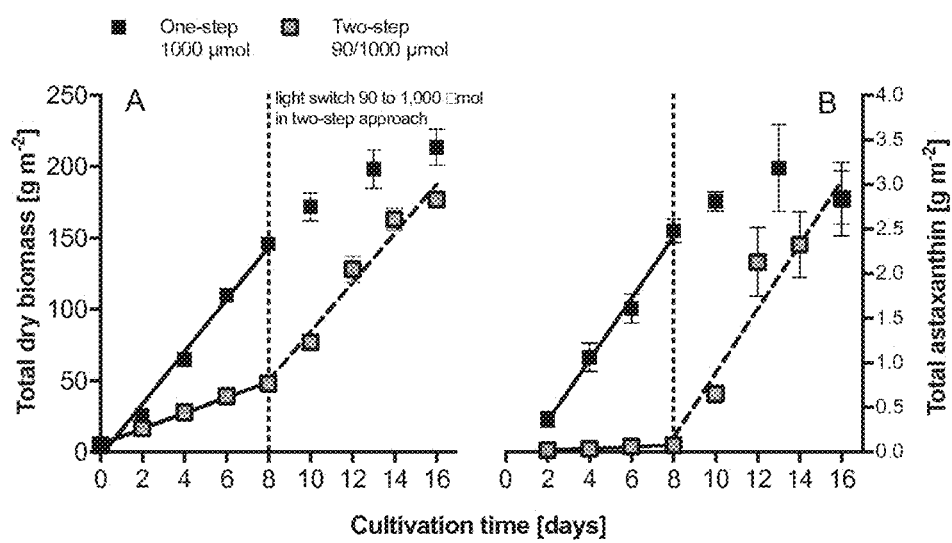

FIG. 3 compares biomass (g m-2) and astaxanthin (g m-2) productivity of *H. pluvialis* of a 10 days one-step process as presented here versus a hypothetical PSBR two-step process combining a "green phase" and a "red phase" of 5 days each.

DETAILED DESCRIPTION OF THE INVENTION

Figure 1:
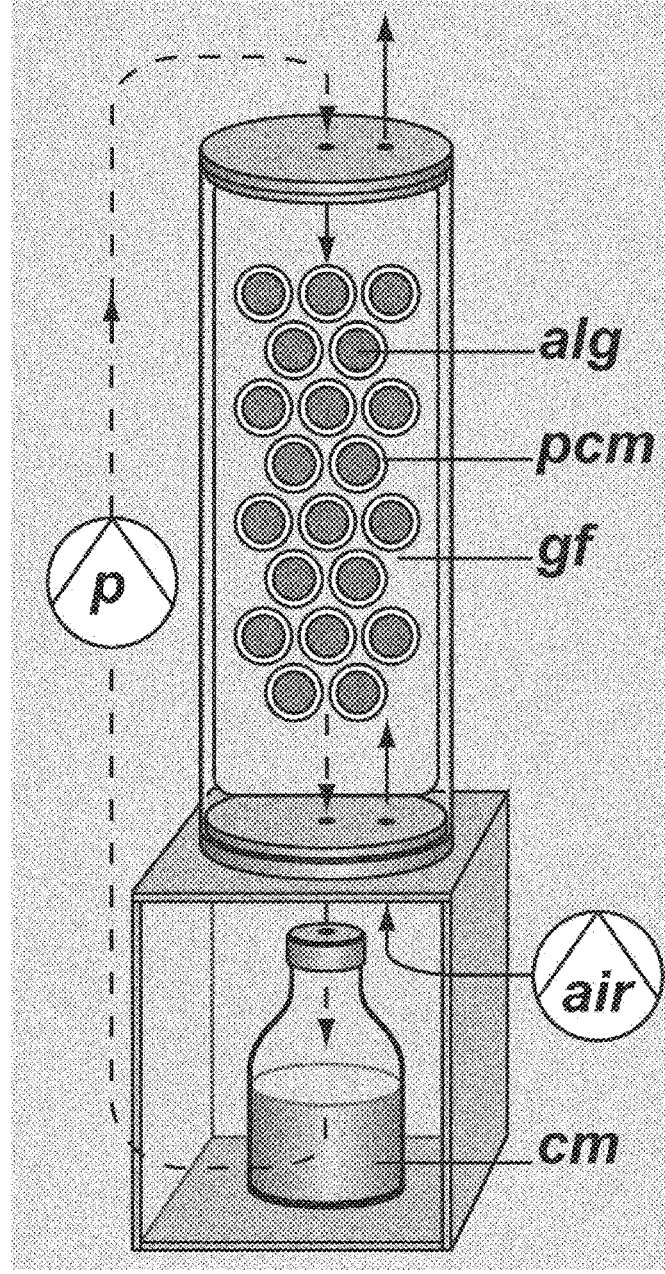
FIG. 1 DEPICTS A LABORATORY-SCALE TWIN-LAYER TEST TUBE.

In WO 2005/010140 A1 a particularly useful method of cultivating microalgae in a biofilm, their growth, and harvesting of astaxanthin is described, in particular a porous substrate for use in the present invention. This reference is incorporated by reference. FIG. 1 depicts a laboratory-scale Twin-Layer test tube. alg—immobilized microalgae, pcm—polycarbonate membrane as a carrier for microalgae, gf—glass fiber mat, air membrane pump for air supply, cm—culture medium as presented by Schultze et al. (2015) to cultivate microalgae in biofilms under various light and $CO_2$ conditions. Other laboratory-scale modifications of porous substrate bioreactors realizing the principle described in WO 2005/010140 A1 were described by Liu et al. (2013); Murphy et al. (2012); Nowack et al. (2005), incorporated by reference.

Scaled up developments of this particular technology offering up to a few square meter substrate surface for biofilm cultivation were described by Naumann et al. (2013) and Zhang et al. (2015), all incorporated by reference.

*H. pluvialis* was grown using porous substrate bioreactors at low light intensities using devices presented by Zhang et al. (2014), Wan et al. (2014) and Yin et al. (2015), all incorporated by reference.

Instead of cultivating *H. pluvialis* in these variations of porous substrate bioreactors, *H. pluvialis* can be grown immobilized in a biofilm on other substrate, which do not display two major surfaces. This can be plastic or concrete structures, etc., which are supplied with culture medium applied on the surface of the biofilm.

Figure 2:
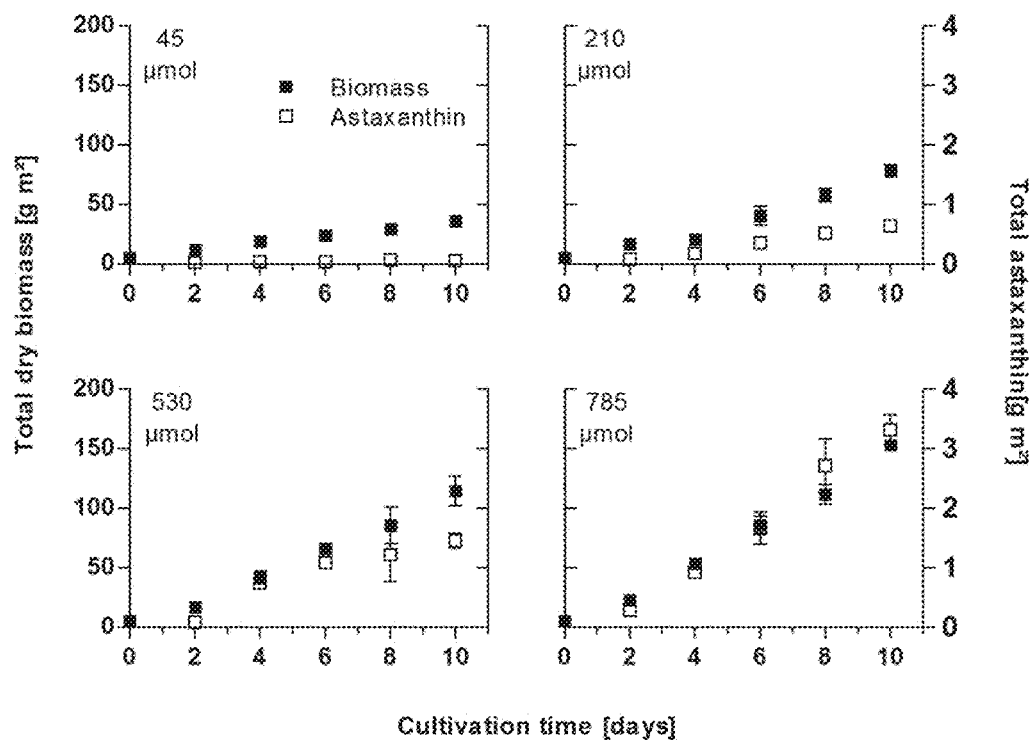
FIG. 2 shows biomass and astaxanthin production by *H. pluvialis* cultivated at different light intensities.

By use of these cultivation procedures, *H. pluvialis* can be cultivated and subjected to high light intensities, FIG. 2 shows cultivation of *H. pluvialis* at different light levels with 5% of supplementary $CO_2$ in an experiment as described in Example 1 below. At low light intensities of 45 µmol $m^{-2}$ $s^{-1}$ (comparable to the green phase of suspension cultivation) no astaxanthin production and only a moderate biomass productivity is reached. High light intensities of about 530 and 785 µmol $m^{-2}$ $s^{-1}$ resulted in an increased biomass and astaxanthin productivity in parallel, showing that (i) astaxanthin induction by high light does not impair growth as observed in suspension-type bioreactors, and (ii) production of astaxanthin can be performed in a continuous one step process, which does not suffer from non-productive (green) growth phases. Highest astaxanthin productivities were reached at 785 µmol $m^{-2}$ $s^{-1}$. High light induced a total astaxanthin productivity of about 0.39 g astaxanthin $m^{-2}$ $d^{-1}$, which was linear during the experimental period and reached 3.3 g $m^{-2}$ after 10 d of growth. At longer cultivation periods, astaxanthin can be higher than 4 g $m^{-2}$, and at higher light intensities of 1,013 µmol $m^{-2}$ $s^{-1}$, astaxanthin productivity is still as high as 0.32 g $m^{-2}$ $d^{-1}$ (data not shown). A hypothetic two-stage scenario was constructed to compare productivity to the one-stage system according to the invention.

FIG. 3 compares biomass (g $m^{-2}$±SD, n=3; FIG. 3A) and total astaxanthin (g $m^{-2}$±SD, n=3; FIG. 3B) productivity of *H. pluvialis* of a 16 days one-step process as presented here versus a PSBR two-step process combining a "green phase" and a "red phase" of 8 days each in order to compare the efficiency of one and two-phase approaches when light is the only applied stress factor. The one-phase approach consisted of exposure to 1,000 µmol photons $m^{-2}$ for 16 days (black squares), whereas the two-phase consisted of 8 days at 90 µmol photons $m^{-2}$ $s^{-1}$ and 8 days at 1,000 µmol photons $m^{-2}$ (grey squares). Vertical dotted line indicates when light intensity was switched for the two-phase approach. Light/dark cycle was 14/10 hours and aeration was supplemented with 5% $CO_2$ during the whole cultivation period. Biomass increased linearly in each phase of cultivation, but at very different rates (FIG. 3A). A growth rate of 5.4 g $m^{-2}$ $d^{-1}$ was observed at low light and it increased to 17.2 g $m^{-2}$ $d^{-1}$ when switched to high light. This value was similar to that obtained during the first 8 days of cultivation directly at 1,000 µmol photons $m^{-2}$ $s^{-1}$ in the one-phase approach. Also, at day 8, standing crop was three fold higher in the one-phase approach, with the value of 146 g $m^{-2}$, when compared to 48.2 g $m^{-2}$ of the two-phase. Similar trends were observed when analysing total astaxanthin values:

Accumulation in the two-phase group only occurred at high light, in a similar rate to that observed for the first eight days of the one-phase: 0.34 and 0.35 g m$^{-2}$ d$^{-1}$, respectively (FIG. 8B). At day 8, astaxanthin yield was 2.5 g m$^{-2}$ at 1,000 μmol photons m$^{-2}$s$^{-1}$ and 0.08 g m$^{-2}$ at 90 μmol photons m$^{-2}$ s$^{-1}$, which results in a 32-fold increase. This difference was abolished after the exposure to high light and astaxanthin production reached 2.8 g m$^{-2}$ in both groups at day 16. However, in the two-phase system it required twice as long as in the one-phase approach. The effect of the high irradiance was, therefore, independent of the beginning of the exposure. That is, the use of a low light green phase hindered the high productivities, requiring a longer cultivation period to reach similar yields, which increases costs and contamination risks.

According to the invention, after cultivation, *H. pluvialis* can be loosened from the support, in particular a perforated support, by the effect of mechanical forces such as scraping or detachment by an air blade or other suitable tools to blow off materials, or, by chemical treatment such as a treatment with surfactants and/or organic solvents.

In another embodiment, the *H. pluvialis* can be harvested together with the perforated support. This may be practical if the *H. pluvialis* are decomposed remaining on the support so as to obtain ingredients by extraction, for example. The extracted *H. pluvialis* or cellular debris can be separated mechanically from the extract together with the support.

In yet another embodiment, (low) volumes of liquid (e.g. water, culture medium) can be used to wash off the immobilized *H. pluvialis* from the perforated support, obtaining a dense suspension of *H. pluvialis* for further processing (concentration, drying, and/or extraction of astaxanthin) or *H. pluvialis* may be obtained by collecting loosened biomass in flowing culture medium.

In particular, *H. pluvialis* can be loosened from the support after drying and may then be collected.

In another embodiment, *H. pluvialis* can be loosened from the support and used after drying or without drying, or without extraction of astaxanthin.

In still another embodiment, extraction of astaxanthin can be performed by treatment with chemicals such as solvents in particular organic solvents, when *H. pluvialis* remains on the substrate and astaxanthin is removed from *H. pluvialis* with the chemicals.

In particular, extraction of astaxanthin from dried or concentrated *H. pluvialis* cells can be performed by methods utilizing organic solvents (Dong et al., 2014) such as hydrochloric acid pretreatment followed by acetone extraction, hexane/isopropanol mixture solvent extraction, methanolic extraction followed by acetone extraction, or by other natural oils such as soy-oil or palm oil. Astaxanthin furthermore can be obtained by supercritical extraction using carbon dioxide (e.g. Nobre. et al., 2006) following to crushing of *H. pluvialis* cells.

The invention is described by the following non-limiting examples.

EXAMPLE 1

Experimental Setup
Bench Scale Biofilm Photobioreactors

The bench scale Twin-Layer photobioreactor (PBR) used was described by Schultze et al (2015), incorporated by reference. Briefly, the system consists of a glass fibre mat (50×10 cm) placed vertically inside a transparent PMMA tube (50 cm long, 12 cm diameter) on a polyvinylchloride (PVC) support. Culture medium is constantly circulated by a peristaltic pump. It is applied at the top of the glass fibre, spreading down with gravity and returning to the medium reservoir, placed inside the PVC support. The system is supplied with 1 L of culture medium which is exchanged every 2-3 days to avoid nutrient limitation for algal growth. Aeration is supplied inside the PVC tube.

For the inoculation of the bioreactor, *H. pluvialis* suspension cultures were concentrated and then filtrated onto polycarbonate membranes (PC40, 0.4 μm pore size, 25 mm diameter, Whatman, Dassel, Germany) as described by Naumann et al (2013), incorporated by reference, to obtain an initial biomass density of 5 g m$^{-2}$. Filters were then placed on the wet glass fibre mats on the PBRs.

For the one-step approach, nutrient-rich culture medium was used throughout the experimental period and different light intensities were evaluated. For comparison, a two-step experiment at low light was performed. Complete culture medium was initially used for growth. After 6 days the stress was induced by changing the medium, namely leaving out the nitrogen source and/or additional salt (0.8%).

Sampling and Determination of Dry Weight

At each sampling point, at least three filters were collected from each PBR. Biomass that had overgrown the inoculation area was removed and the filter was freeze dried to constant weight. Dry weight was determined gravimetrically and biomass was stored at −20° C. until astaxanthin analysis.

Astaxanthin Determination

Astaxanthin was determined spectrophotometrically as described by Li et al (2012). Freeze dried biomass samples were extracted with Dimethyl sulfoxide (DMSO, Merck, Darmstadt, Germany), incubated at 70° C. for 5 minutes then centrifuged at 4000 g for 5 minutes. Extraction was repeated until a colourless pellet was obtained. Supernatants were collected and the OD was measured at 530 nm (Infinite M200 plate reader, Tecan, Männedorf, Switzerland). When necessary for complete extraction, cells were broken by grinding with sand. Astaxanthin concentration was determined based on a calibration curve constructed with astaxanthin standard (98.6% purity, Dr. Ehrenstorfer, Ausburg, Germany) dissolved and diluted in DMSO.

Furthermore, other artificial or natural culture media which are suitable to promote microalgal growth can be used for *H. pluvialis* cultivation.

Supplementary $CO_2$ is advantageous to promote biomass growth in particular under high light conditions, however, is not essential.

Light sources, in general can be artificial illumination and use of natural sunlight, whereas the use of sunlight may be preferred for economic reasons (in particular if high intensities are required).

REFERENCES

Aflalo C, Meshulam Y, Zarka A, Boussiba S (2007) On the Relative Efficiency of Two-vs. One-stage Production of Astaxanthin by the Green Alga *Haematococcus pluvialis*. Biotechnol Bioeng 98:300-305. doi: 10.1002/bit.21391

Berner F, Heimann K, Sheehan M (2014) Microalgal biofilms for biomass production. J Appl Phycol. doi: 10.1007/s10811-014-0489-x Del Rio E, Acién F G, Garcia-Malec M C, et al (2005) Efficient one-step production of astaxanthin by the microalga *Haematococcus pluvialis* in continuous culture. Biotechnol Bioeng 91:808-815. doi: 10.1002/bit.20547

Dong, S., Huang, Y., Zhang, R., Wang, S., & Liu, Y. (2014). Four Different Methods Comparison for Extraction of Astaxanthin from Green Alga *Haematococcus pluvialis*, 2014

Fiedler, D., Hager, U., Franke, H., Soltmann, U., Böttcher, H., (2007) Algae biocers: astaxanthin formation in sol-gel immobilised living microalgae. J. Mater. Chem. 2007, 17, 261-266

Garcia-Malea López M C, Sánchez F D R, Casas López J L, et al (2006) Comparative analysis of the outdoor culture of *Haematococcus pluvialis* in tubular and bubble column photobioreactors, J Biotechnol 123:329-342. doi: 10.1016/j.jbiotec.2005.1.1.010

Li Y, Miao F, Geng Y, et al (2012) Accurate quantification of astaxanthin from *Haematococcus* crude extract spectrophotometrically. Chinese J Oceanol Limnol 30:627-637. doi: 10.1007/s00343-012-1217-5

Liu T, Wang J, Hu Q, et al (2013) Attached cultivation technology of microalgae for efficient biomass feedstock production. Bioresour Technol 127:216-222. doi: 10.1016/j.biortech.2012.09.100

Lorenz R T, Cysewski G R (2000) Commercial potential for *Haematococcus* microalgae as a natural source of astaxanthin. Trends Biotechnol 18:160-167.

Murphy T, Fleming E, Bebout L, et al (2012) A Novel Microbial Cell Cultivation Platform for Space Applications. In: 1st Annual International Space Station Research and Develop-ment Conference. Denver, CO: American Astronomical Society (AAS). pp 335-339

Naumann T, Cebi Z, Podola B, Melkonian M (2013) Growing microalgae as aquaculture feeds on twin-layers: a novel solid-state photobioreactor. J Appl Phycol 25:1413-1420. doi: 10.1007/s10811-012-9962-6

Nguyen K (2013) Astaxanthin: a comparative case of synthetic vs. natural production. Chem Biomol Eng Publ Other Work 1:1-11.

Nobre, B., Marcelo, F., Passes, R., Beirao, L., Palavra, A., Gouveia, L., & Mendes, R. (2006). Supercritical carbon dioxide extraction of astaxanthin and other carotenoids from the microalga *Haematococcus pluvialis*: European Food Research and Technology, 223, 787-790. Retrieved from dx.doi.org/10.1007/s00217-006-0270-8

Nowack E C M, Podola B, Melkonian M (2005) The 96-well Twin-Layer system: A novel approach in the cultivation of microalgae. Protist 156:239-251. doi: 10.1016/j.protis.2005.04.003

Olivieri G, Salatino P, Marzocchella A (2014) Advances in photobioreactors for intensive microalgal production: configurations, operating strategies and applications. J Chem Technol Biotechnol 89:178-195. doi: 10.1002/jctb.4218

Ozkan A, Kinney K, Katz L, Berberoglu H (2012) Reduction of water and energy requirement of algae cultivation using an algae biofilm photobioreactor. Bioresour Technol 114:542-8, doi: 10.1016/j.biortech.2012.03.055

Schultze L K P, Simon M-V, Li T, et al (2015) High light and carbon dioxide optimize surface productivity in a Twin-Layer biofilm photobioreactor. Algal Res 8C:37-44. doi: 10.1016/j.algal.2015.01.007

Suh I S, Joo H-N, Lee C-G (2006) A novel double-layered photobioreactor for simultaneous *Haematococcus pluvialis* cell growth and astaxanthin accumulation. J Biotechnol 125:540-6. doi: 10.1016/j.Thiotec.2006.03.027

Wan M, Hou D, Li Y, et al (2014) The effective photoinduction of *Haematococcus pluvialis* for accumulating astaxanthin with attached cultivation. Bioresour Technol 163C: 26-32. doi: 10.1016/j.biortech.2014.04.017

Wang J, Sommerfeld M R, Lu C, Hu Q (2013) Combined effect of initial biomass density and nitrogen concentration on growth and astaxanthin production of. Algae 28:193-202.

Yin S, Wang J, Chen L, Liu T (2015) The water footprint of biofilm cultivation of *Haematococcus pluvialis* is greatly decreased by using sealed narrow chambers combined with slow aeration rate. Biotechnol Lett. doi: 10.1007/s10529-015-1864-7

Zhang L, Chen L, Wang J, et al (2015) Attached cultivation for improving the biomass productivity of Spirulina platensis. Bioresour Technol 181:136-442. doi: 10.1016/j.biortech.2015.01.025

Zhanq W, Wang J J, Wang J J, Liu T (2014) Attached cultivation of *Haematococcus pluvialis* for astaxanthin production. Bioresour Technol 158C:329-335. doi: 10.1016/j.biortech.2014.02.044

The invention claimed is:

1. A method for an improved astaxanthin production, the method comprising:
   providing a substrate;
   arranging the *Haematococcus* species on surface of the substrate to form a biofilm
   cultivating the biofilm of *Haematococcus* species on the substrate at a high light intensity to increase biomass productivity and to induce and to increase astaxanthin production at the same time,
   wherein the high light intensity is 250 µmol photons $m^{-2}$ $s^{-1}$ or more.

2. The method of claim 1, further comprising harvesting the cultured *Haematococcus* species and isolating the astaxanthin from the harvested *Haematococcus* species.

3. The method of claim 1, wherein the *Haematococcus* species is *Haematococcus pluvialis*.

4. The method of claim 1, wherein the substrate is a sheet-like material.

5. The method of claim 4, wherein the substrate is a porous sheet.

6. The method of claim 4, wherein the sheet-like material is selected from the group consisting of paper, cellulose ester, mixed cellulose ester, cellulose, cellulose nitrate, polyamides, polyesters and polyolefins.

7. The method of claim 1, wherein cultivating the biofilm of *Haematococcus* species comprises a light/dark cycle of 14/10 hours is used in combination with 5% $CO_2$ during the cultivation.

8. The method of claim 1, wherein the astaxanthin is present in an amount higher than 4 g $m^{-2}$ prior to harvesting.

9. The method of claim 1, wherein the process does not include a low-light exposure, wherein low light is 50 µmol photons $m^{-2}$ $s^{-1}$ to less than 200 µmol photons $m^{-2}$ $s^{-1}$.

10. The method of claim 1, wherein high light intensity is 500 µmol photons $-m^{-2}$ $s^{-1}$ or more.

* * * * *